United States Patent [19]

Parker et al.

[11] Patent Number: 5,225,586
[45] Date of Patent: Jul. 6, 1993

[54] BENZOCYCLOBUTENE CAPPED FLUOROALKYL AROMATIC BASED FLUOROARYLETHER MONOMERS, OLIGOMERS, AND REACTION PRODUCTS

[75] Inventors: Theodore L. Parker; Thomas W. Regulski, both of Walnut Creek, Calif.

[73] Assignee: The Dow Chemical Company, Midland, Mich.

[21] Appl. No.: 759,313

[22] Filed: Sep. 13, 1991

[51] Int. Cl.$^5$ .................... G07C 205/00; G07C 41/00
[52] U.S. Cl. ........................ 560/21; 560/24; 560/25; 560/26; 560/27; 560/28; 560/30; 560/31; 560/33; 560/56; 560/59; 560/63; 560/65; 560/80; 560/83; 568/20; 568/23; 568/24; 568/25; 568/337; 568/631; 568/632; 568/633; 568/634

[58] Field of Search .............. 568/20, 23, 24, 25, 568/337, 631, 632, 633, 634; 560/21, 24, 25, 26, 27, 28, 30, 31, 33, 56, 59, 63, 65, 80, 83

[56] References Cited

U.S. PATENT DOCUMENTS

| | | |
|---|---|---|
| 4,540,763 | 9/1985 | Kirchhoff . |
| 4,638,078 | 1/1987 | Kirchhoff . |
| 4,642,329 | 2/1987 | Kirchhoff et al. . |
| 4,687,823 | 8/1987 | Kirchhoff et al. . |
| 4,783,514 | 11/1988 | Kirchhoff et al. . |
| 4,825,001 | 4/1989 | Bruza et al. . |
| 5,030,252 | 7/1991 | Sanders, Jr. et al. . |

*Primary Examiner*—José G. Dees
*Assistant Examiner*—Keith MacMillan

[57] ABSTRACT

The invention relates to benzocyclobutene capped benzotrifluoride based fluoroaryl ether compounds which are useful in preparing semi-permeable membranes, and films and coatings useful in electronic applications.

6 Claims, No Drawings

BENZOCYCLOBUTENE CAPPED FLUOROALKYL AROMATIC BASED FLUOROARYLETHER MONOMERS, OLIGOMERS, AND REACTION PRODUCTS

BACKGROUND OF THE INVENTION

The invention is a new composition of matter comprising benzocyclobutene functional fluoroaryl ether monomers, oligomers, and reaction products.

Certain organic compounds containing multiple benzocyclobutene (hereinafter referred to as BCB) groups are known to undergo cross-linking reactions when heated, resulting in the formation of network or thermoset systems. Such compounds have utility in various adhesive, composite, and electronic applications. However, many multi-functional BCB compounds are solids having melting points close to the temperature at which the BCB group reacts. These properties limit the usefulness of such compounds in electronic coating applications because there is generally insufficient processing time for such materials to melt and flow to form a uniform, coherent coating before gelation occurs. Furthermore, some BCB materials that are liquids at ambient temperatures have too low a viscosity and must be pretreated or advanced before being used as electronic coatings.

What is needed is a multi-functional BCB composition possessing viscosity characteristics suitable for use as electronic coatings without pretreatment. Such a composition preferably would be a low melting solid or wax having increased viscosity that provides for a longer processing window before cross-linking occurs. The composition should also possess a low dielectric constant and a low water absorption value.

SUMMARY OF THE INVENTION

The invention is a new composition of matter comprising a multi-benzocyclobutene functional fluoroaryl ether compound characterized by having a plurality of benzocyclobutene moieties connected via aromatic ether linkages to aromatic rings substituted with at least one fluoroalkyl moiety and optionally additional fluorine groups.

In another aspect, the invention is a new composition of matter comprising the reaction product of a mixture comprising a benzocyclobutene functional compound additionally containing a phenolic hydroxyl group, a fluoroalkyl aromatic compound containing at least two displaceable aromatic fluorine, chlorine, or nitro groups, and optionally a bisphenolic compound containing two phenolic hydroxyl functionalities.

DETAILED DESCRIPTION OF THE INVENTION

The multi-benzocyclobutene functional fluoroaryl ether compounds of this invention are characterized by having a plurality of benzocyclobutene moieties connected via aromatic ether linkages to aromatic rings substituted with at least one fluoroalkyl moiety and optionally additional fluorine groups. Optionally, the fluoroalkyl-substituted aromatic rings may also be joined to one another via ether linkages comprising other divalent aromatic residues which may optionally be further substituted through ether linkages with groups containing the benzocyclobutene function.

The composition of the present invention includes the reaction products of a mixture comprising a benzocyclobutene functional compound additionally containing a phenolic hydroxyl group, a fluoroalkyl aromatic compound containing at least two displaceable aromatic fluorine, chlorine, or nitro groups, and optionally a bisphenolic compound containing two phenolic hydroxyl functionalities.

Preferably, the multi-benzocyclobutene functional fluoroaryl ether compounds of this invention are characterized by the structural formula:

$$(BCB-O)_x\underset{F_w}{\overset{R_z}{\bigcirc}}\left[O-Ar-O\underset{(BCB-O)_y}{\overset{R_z}{\bigcirc}}F_w\right]_r O-BCB,$$

wherein
BCB is a monovalent radical of the formula:

$$\underset{}{\overset{R^1}{\bigcirc}}\!,$$

wherein
$R^1$ is a direct bond or a divalent $C_{1\text{-}4}$ alkyl radical, a divalent $C_{7\text{-}24}$ alkylaryl radical, or a divalent $C_{6\text{-}24}$ aryl radical;

R is a monovalent fluoroalkyl moiety of the formula $C_nF_{2n+1}$, wherein n is an integer between 1 and 8 inclusive;

Ar is a divalent aromatic residue selected from the group consisting of an unsubstituted or inertly substituted phenylene radical, an unsubstituted or inertly substituted naphthylene radical, a bisphenyl fluorenyl radical, a spiro indanyl radical, and an unsubstituted or inertly substituted bisphenylene radical of the formula:

$$\underset{(X)_m}{\bigcirc}\!-\!L\!-\!\underset{(X)_m}{\bigcirc}$$

wherein
L is selected from the group consisting of a direct bond, a divalent $C_{1\text{-}16}$ hydrocarbyl radical, a divalent $C_{1\text{-}8}$ halohydrocarbyl radical, —O—, —CO—, —CO$_2$—, —CONH—, —S—, —SO—, —SO$_2$—, and —SS—, X is individually in each occurrence selected from the group consisting of a hydrogen radical, a monovalent $C_{1\text{-}4}$ hydrocarbyl radical, a monovalent $C_{1\text{-}4}$ halohydrocarbyl radical, and a halogen, and m is a positive integer between 1 and 4 inclusive; and w is an integer from zero to 3, and z is an integer from 1 to 4, with the proviso that $w+z \leq 4$;

x is an integer from 1 to 4:

y is an integer from zero to 3; and r is an integer from zero to 20.

R is preferably a monovalent fluoroalkyl moiety of the formula $C_nF_{2n+1}$ wherein n is an integer between 1 and 6, inclusive, more preferably between 1 and 4, inclusive.

$R^1$ is preferably a direct bond or a divalent $C_{1-4}$ alkyl radical, a divalent $C_{7-18}$ alkylaryl radical, or a divalent $C_{6-18}$ aryl radical, more preferably a direct bond or a divalent $C_{1-4}$ alkyl radical, a divalent $C_{7-12}$ alkylaryl radical, or a divalent $C_{6-12}$ aryl radical.

Ar is preferably an unsubstituted or inertly substituted bisphenylene radical. When Ar is a bisphenylene radical, L is preferably selected from the group consisting of a direct bond, a divalent $C_{1-16}$ hydrocarbyl radical, and a divalent $C_{1-8}$ halohydrocarbyl radical.

r is preferably an integer between zero and 8, more preferably an integer between 1 and 4.

The hydroxybenzocyclobutenes useful as starting materials for the synthesis of the compounds of this invention may be prepared by methods known in the art. See U.S. Pat. No. 4,937,287, Fleming et al., "The Regioselectivity Of The Diels-Alder Reaction Between A Diene With An Electron-Donating Substituent And A Dienophile With An Electron-Donating Substituent: A Test Case For Frontier Orbital Theory," *Tetrahedron Letters*, No. 11, 1976, pp. 881–884, Schiess et al., "Preparation Of Benzocyclo-butenes By Flash Vacuum Pyrolysis", *Tetrahedron Letters*, No. 46, 1978, pp. 4569–4572, Klundt, "Benzocyclobutene And Its Derivatives," *Chem. Rev.*, No. 70, 1970, pp. 471–472; Finnegan, "Organometallic Chemistry. IX. The Metalation Of Benzocyclobutene With Sodium And Potassium Alkyls," *J. Org. Chem.*, No. 30, 1965, pp. 1333–1335, and Horner et al., "Zur Elektrophilen Substitution Des Benzocyclobutens", *Chemische Berichte Jahrg.*, 93, 1960, pp. 1774–1781, the relevant portions incorporated herein by reference.

The compounds of this invention are prepared from the corresponding fluoroalkyl aromatic halide, hydroxy BCB, and bisphenol by combining in a stirred reactor under an inert atmosphere such as nitrogen all phenolic hydroxy components with a base such as potassium carbonate, sodium hydroxide, potassium hydroxide, or sodium hydride, which is capable of generating the phenoxy anion, in an amount sufficient to generate a slight stoichiometric excess, preferably between about 1.00 and 1.25 equivalents of base per phenolic hydroxyl, more preferably between about 1.00 and about 1.05 equivalents of base per phenolic hydroxyl, in an aprotic solvent such as N-methyl-2-pyrrolidinone, dimethylacetamide, dimethylsulfoxide, dimethylformamide, or N-cyclohexylpyrrolidinone. An azeotroping solvent such as toluene or benzene, in an amount preferably between about 10 percent and about 100 percent by volume of aprotic solvent, more preferably between about 40 percent and about 60 percent by volume of aprotic solvent, is added to the mixture and the water azeotropically removed by distillation by heating for a sufficient period of time. Optionally, dry solvent may be recycled to the reactor. The azeotroping solvent is distilled out of the reactor. The reaction mixture is cooled to about 25° C. to about 100° C. and the fluoroalkyl aromatic component containing at least two phenoxy displaceable groups is added. The reaction temperature is slowly increased to about 100° C. to about 180° C. over a period of time sufficient to allow all the volatile fluoroalkyl aromatic component to be reacted in at least one position to increase the resultant boiling point above the reaction temperature. Generally the temperature is increased stepwise on an appropriate schedule, for example, heating for about 1 hour to about 120° C., about 140° C. for about 1 hour, and about 150° C. for about 1 hour. The reaction mixture is then cooled to below about 75° C. to minimize foaming and is then neutralized with a stoichiometric amount of a weak acid such as acetic acid. A water immiscible co-solvent such as methylene chloride or other halogenated or aromatic organic is then added, then the mixture extracted several times with portions of water sufficient to dissolve and remove all salt by-products. The organic solution is separated and dried with an inorganic drying agent such as anhydrous magnesium sulfate, filtered, and evaporated to yield the BCB product.

The compounds of this invention preferably possess a glass transition temperature (Tg) as measured by Differential Scanning Calorimetry (DSC) scanning at a rate of about 20° C./minute in the range of about 25° C. to about 180° C. The compounds preferably possess a tensile strength as measured by ASTM D-1708 in the range of about 3 kpsi ($2.1 \times 10^4$ kPa) to about 12 kpsi ($8.3 \times 10^4$ kPa). The compounds preferably possess a tensile modulus as measured by ASTM D-1708 in the range of about 150 kpsi ($1.0 \times 10^6$ kPa) to about 400 kpsi ($2.8 \times 10^6$ kPa). The compounds preferably possess an elongation at break as measured by ASTM D-1708 of between about 1 percent and about 10 percent. The compounds preferably exhibit a decomposition temperature ($T_d$) at 10 percent weight loss as measured by Thermogravimetric Analysis (TGA) scanning at a rate of about 10° C./minute in nitrogen of at least about 400° C. The compounds preferably possess a dielectric constant of between about 2.5 and about 3.5.

The compounds of this invention are useful as electronic coatings and as gas separation membrane discriminating layers.

To form films or coatings, the compounds are dissolved in a solvent such as toluene. The solution is then cast, coated, sprayed, dipped, or otherwise applied to a substrate. The films or coatings are cured by preferably heating stepwise at about 220° C. to about 250° C. for a period of time sufficient to substantially complete the cross-linking reaction, generally about 1 hour to about 6 hours. The resulting cross-linked network is substantially insoluble in solvents such as toluene and methylene chloride.

DETAILED EMBODIMENTS

The following Example is for purposes of illustration and is not intended to limit the scope of the invention or claims.

EXAMPLE - BENZOCYCLOBUTENE (BCB) CAPPED HEPTAFLUOROTOLUENE (HFT) BASED MONOMER AND OLIGOMERS

Preparation of Bis (Benzocyclobutenyloxy) pentafluorotoluene

A 250 milliliter three necked round bottomed flask equipped with a mechanical stirrer, thermocouple controller probe, gas inlet and outlet, and Dean-Stark apparatus was charged with N-methyl-2-pyrrolidinone (NMP) solvent, about 80 milliliters, and toluene, about 65 milliliters, and the flask was purged with a slow nitrogen stream and the mixture stirred. 4-Hydroxybenzocyclobutene, about 7.50 grams (about 62.43 mmole), and ground anhydrous potassium carbonate, about 8.97 grams (about 64.9 mmole), were added to the mixture and heating begun. Water was azeotropically removed into the Dean-Stark apparatus at about 145° C. to 150° C. over about 25 minutes. The nitrogen flow was increased and toluene was distilled out at about 160° C. over about 15 minutes. The reaction mixture was then cooled in a water bath to about 50° C. The heating mantle was replaced, and a,a,a,2,3,5,6-heptafluorotoluene, about 6.81 grams (about 31.22 mmole), was added in one portion and heating resumed. The reaction mixture was held at about 120° C. for about 2 hours, then at about 140° C. for about 1 hour, and finally at about 150° C. for about 1 hour. After cooling to ambient temperature, the reaction mixture was neutralized with about 3.9 grams glacial acetic acid, diluted with about 100 milliliters methylene chloride, then transferred to a separatory funnel. The reaction mixture was extracted with about 500 milliliters of water divided into five portions, then the organic layer was dried over anhydrous magnesium sulfate, filtered through a fine glass frit, and the filtrate placed in a crystallizing dish on a hot plate with a surface temperature of about 125° C. for about 1 hour. The resultant yellow oil was allowed to cool and solidify to give a waxy product, about 12.75 grams, representing about 91 percent of theoretical yield. The waxy product was then triturated with 50/50 v/v methanol/water to give an amorphous powder. Melting point by Differential Scanning Calorimetry (DSC) was about 106° C. Analysis by fluorine-19 nmr indicated the product was composed of about 70 mole percent disubstituted 2,6-isomer, about 26 mole percent disubstituted 2,5-isomer, and about 4 mole percent trisubstituted 2,3,6-isomer.

Preparation of Benzocyclobutene (BCB) Capped Heptafluorotoluene (HFT)/Bis AF Oligomer (n=1)

A 1 liter three necked round bottomed flask equipped with a mechanical stirrer, thermocouple controller probe, gas inlet and outlet, and Dean-Stark apparatus was charged with N-methyl-2-pyrrolidinone (NMP) solvent, about 320 milliliters, and toluene, about 205 milliliters. The flask was purged with a slow nitrogen stream for about 10 minutes while stirring the mixture. 4-Hydroxybenzocyclobutene, about 14.24 grams (about 118.55 mmole), bis 2,2-(4-hydroxyphenyl)-1,1,1,3,3,3-hexafluoropropane (Bis AF), about 19.93 grams (about 59.26 mmole), and ground anhydrous potassium carbonate, about 34.40 grams (about 249.3 mmole), were added to the mixture and heating begun. Water was azeotropically removed into the Dean-Stark apparatus at about 145° C. to about 150° C. over about 30 minutes. The nitrogen flow was increased and toluene was distilled out at about 165° C. over about 35 minutes. The reaction mixture was then cooled in a water bath to about 65° C. The heating mantle was replaced, a,a,a,2,3,5,6-heptafluorotoluene, about 25.85 grams (about 118.54 mmole), was added in one portion and heating resumed. The reaction mixture was held at about 120° C. for about 1 hour, then at about 140° C. for about 1 and ½ hours, and at about 150° C. for about 1 hour. After cooling to about 65° C., the reaction mixture was neutralized with about 15.0 grams glacial acetic acid, then filtered through a fine glass frit and precipitate washed twice with about 90 milliliter portions of methylene chloride, which was combined with filtrate. About 100 milliliters more methylene chloride was added and the organic layer extracted with about 1000 milliliters of water divided into 5 portions. The organic layer was dried over anhydrous magnesium sulfate and filtered through a fine glass frit. The filtrate was vacuum stripped at about 130° C. to give a hard resinous product after cooling, about 37.9 grams. The glass transition temperature (Tg) as measured by DSC inflection point was about 68° C.

Preparation of Benzocyclobutene (BCB) Capped Heptafluorotoluene (HFT)/Bis AF Oligomer (n=2)

A 2 liter three necked round bottomed flask equipped with a mechanical stirrer, thermocouple controller probe, gas inlet and outlet, and Dean-Stark apparatus was charged with N-methyl-2-pyrrolidinone (NMP) solvent, about 400 milliliters, and toluene, about 225 milliliters, and purged with a slow nitrogen stream for about 10 minutes while stirring. 4-Hydroxybenzocyclobutene, about 11.51 grams (about 95.77 mmole), bis 2,2-(4-hydroxyphenyl)-1,1,1,3,3,3-hexafluoropropane (Bis AF), about 32.19 grams (about 95.72 mmole), and ground anhydrous potassium carbonate, about 76.6 grams (about 555 mmole), were added and heating commenced. Water was azeotropically removed into the Dean-Stark apparatus at about 145° C. to 150° C. over about 30 minutes. The nitrogen flow was increased and toluene was distilled out at about 160° C. over about 35 minutes. The reaction mixture was then cooled in a water bath to about 50° C. The heating mantle was replaced, a,a,a,2,3,5,6-heptafluorotoluene, about 31.31 grams (about 143.60 mmole), was added in one portion and heating resumed. The reaction mixture was held at about 120° C. for about 1 hour, at about 140° C. for about 1 and ½ hours, and finally at about 150° C. for about 1 hour. After cooling to about 60° C., the reaction mixture was neutralized with about 49.2 grams glacial acetic acid, then filtered through a fine glass frit and precipitate washed with about 400 milliliters of methylene chloride divided into four portions, which was combined with filtrate in separatory funnel. The organic layer was extracted with about 1600 milliliters of water divided into four portions. The organic layer was dried over anhydrous magnesium sulfate, filtered through a fine glass frit, and the filtrate vacuum stripped at about 165° C. to give a hard resinous product after cooling, about 59.5 grams, representing about an 86 percent theoretical yield. The glass transition temperature (Tg) as measured by DSC inflection point was about 73° C.

Preparation of Benzocyclobutene (BCB) Capped Heptafluorotoluene (HFT)/Bis AF Oligomer (n=4)

A 2 liter three necked round bottomed flask equipped with a mechanical stirrer, thermocouple controller probe, gas inlet and outlet, and Dean-Stark apparatus was charged with N,N-dimethylacetamide (DMAc) solvent, about 400 milliliters, and toluene, about 225 milliliters, and purged with a slow nitrogen stream for about 10 minutes while stirring. 4-Hydroxybenzocyclobutene, about 6.01 grams (about 50.01 mmole), bis 2,2-(4-hydroxyphenyl)-1,1,1,3,3,3-hexafluoropropane (Bis AF), about 33.62 grams (about 99.99 mmole), and ground anhydrous potassium carbonate, about 36.52 grams (about 265 mmole), were added and heating commenced. Water was azeotropically removed into the Dean-Stark apparatus at about 135° C. to about 140° C. over about 45 minutes. The nitrogen flow was increased and toluene was distilled out at about 155° C. over about 15 minutes. The reaction mixture was then cooled in a water bath to about 60° C. The heating mantle was replaced, a,a,a,2,3,5,6-heptafluorotoluene, about 27.26 grams (about 124.99 mmole), was added in one portion and heating resumed. The reaction mixture was held at about 120° C. for about 1 hour and at about 140° C. for about ½ hour. After cooling to about 60° C., the reaction mixture was neutralized with about 16.0 grams glacial acetic acid, then about 400 milliliters water containing about 2 grams concentrated hydrochloric acid was added. The reaction mixture was transferred to a separatory funnel containing about 400 milliliters methylene chloride. The mixture was separated and the organic layer extracted with about 1600 milliliters of water divided into four portions. The organic layer was dried over anhydrous magnesium sulfate, filtered through a fine glass frit, and the filtrate vacuum stripped at about 175° C. over about 25 minutes to give a hard resinous product after cooling, about 57.80 grams, representing about a 77 percent theoretical yield. The glass transition temperature (Tg) as measured by DSC inflection point was about 86° C.

Cure of Benzocyclobutene (BCB) Capped Heptafluorotoluene (HFT)/Bis AF Oligomer Films and Membranes Solutions in toluene were prepared containing about 40 to 70 percent by weight of the various oligomers (n=1, 2, and 4). A casting bar with a 0.015 inch (0.038 centimeter) clearance was used to cast films onto a substrate of 0.005 inch (0.013 centimeter) thick aluminum stock. The cast films were allowed to air dry, then residual solvent removed by heating at about 70° C. to 120° C. in a forced air oven. The samples were transferred to a vacuum oven preheated to about 190° C., then cured under full vacuum according to the following schedule: about 1 hour at about 190° C., and about 2 hours at about 220° C., and about 1 hour at about 250° C. The aluminum substrate was then dissolved away by floating the sample on 5 to 10 percent by weight hydrochloric acid, then water washing the surface. The glass transition temperatures (Tg) of the cured samples were determined by the inflection point of a Differential Scanning Calorimetry (DSC) plot run at a rate of about 20° C./minute. Thermogravimetric Analysis (TGA) was conducted at a scan rate of about 10° C./minute under both air and nitrogen, and the decomposition temperature (Td) at 10 percent weight loss determined. A duPont 1090 Thermal Analyzer was used for both the DSC and TGA determinations. The dielectric constant was measured by a Hewlett-Packard 4284 LCR meter using the two fluid technique with LD3 cell. Data are reported in Table IA.

TABLE IA

| Sample n= | Uncured $T_g$ (°C.) | Cured $T_g$ (°C.) | $T_d$ Air (°C.) | $T_d$ $N_2$ (°C.) | Dielectric Constant[1] |
|---|---|---|---|---|---|
| 0 | 105[2] | 349 | — | 463 | 2.67 |
| 1 | 68 | 213 | 515 | 504 | 2.57 |
| 2 | 73 | 203 | 513 | 507 | 2.57 |
| 4 | 85 | 176 | 517 | 514 | — |

[1]Dielectric Constant at 100 kHz
[2]Melting Point

Physical Properties of Cured Benzocyclobutene (BCB) Capped Heptafluorotoluene (HFT)/Bis AF Oligomer Films Specimens measuring about 0.5 inches (1.27 centimeters) by about 2.5 inches (6.35 centimeters) were prepared from the film samples. The specimens were pulled at about 0.4 inches/minute (1.02 centimeters/minute) on an Instron machine to determine the stressstrain behavior reported in Table IB.

TABLE IB

| Sample n= | Tensile Strength | | Tensile Module | | Elongation at Failure |
|---|---|---|---|---|---|
| | (psi) | (kPa) | (kpsi) | (kPa) | (percent) |
| 1 | 9684 | $6.68 \times 10^4$ | 340.8 | $2.35 \times 10^6$ | 4.2 |
| 2 | 6283 | $4.33 \times 10^4$ | 309.8 | $2.14 \times 10^6$ | 2.7 |

Membrane Properties of Cured Benzocyclobutene (BCB) Capped Heptafluorotoluene (HFT)/Bis AF Oligomers The film samples were evaluated for gas separation properties using a constant-volume, variable-pressure gas permeability apparatus. The pure gas permeabilities for helium, methane, ethane, ethylene, oxygen, and nitrogen were measured at about 30° C. and the gas selectivities calculated therefrom. Data are reported in Table IC. Comparative data for a membrane prepared from the homopolymer prepared from heptafluorotoluene and bisphenol AF, that is, (oxy-2,2-bis(4,4′-phenylene)-1,1,1,3,3,3-hexafluoropropane-oxy-2,6-(trifluoromethyl phenylene), is also illustrated in Table IC.

TABLE IC

| Sample n= | Permeability (Barrers) | | Separation Factor | | | |
|---|---|---|---|---|---|---|
| | He | $O_2$ | He/$CH_4$ | He/$C_2H_4$ | He/$C_2H_6$ | $O_2$/$N_2$ |
| 1 | 56 | 4.2 | 130 | 185 | 590 | 4.8 |
| 2 | 74 | 5.7 | 155 | 165 | 630 | 5.5 |
| Poly | 190 | 26 | 9 | 9 | 10 | 1.7 |

What is claimed is:

1. A compound comprising a multi-benzocyclobutene functional fluoroaryl ether characterized by the structural formula:

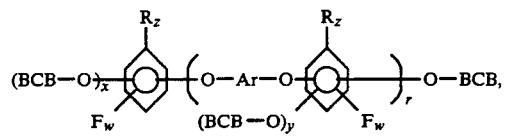

wherein
BCB is a monovalent radical of the formula:

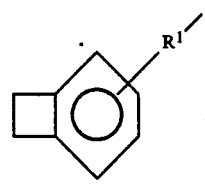

wherein
$R^1$ is a direct bond or a divalent $C_{1-4}$ alkyl radical, a divalent $C_{7-24}$ alkylaryl radical, or a divalent $C_{6-24}$ aryl radical;
R is a monovalent fluoroalkyl moiety of the formula $C_nF_{2n+1}$, wherein n is an integer between 1 and 8 inclusive;

Ar is a divalent aromatic residue selected from the group consisting of an unsubstituted or inertly substituted phenylene radical, an unsubstituted or inertly substituted naphthylene radical, a bisphenyl fluorenyl radical, a spiro indanyl radical, and an unsubstituted or inertly substituted bisphenylene radical of the formula:

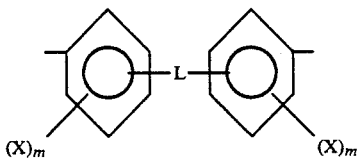

wherein
L is selected from the group consisting of a direct bond, a divalent $C_{1-16}$ hydrocarbyl radical, a divalent $C_{1-8}$ halohydrocarbyl radical, —O—, —CO—, —CO$_2$—, —CONH—, —S—, —SO—, —SO$_2$—, and —SS—,
X is individually in each occurrence selected from the group consisting of a hydrogen radical, a monovalent $C_{1-4}$ hydrocarbyl radical, a monovalent $C_{1-4}$ halohydrocarbyl radical, and a halogen, and
m is a positive integer between 1 and 4 inclusive; and
w is an integer from zero to 3, and
z is an integer from 1 to 4, with the proviso that $w+z \leq 4$;
x is an integer from 1 to 4:
y is an integer from zero to 3; and
r is an integer from zero to 20.

2. The compound of claim 1 wherein R is a monovalent fluoroalkyl moiety of the formula $C_nF_{2n+1}$ wherein n is an integer between 1 and 6, inclusive.

3. The compound of claim 2 wherein $R^1$ is a direct bond or a divalent $C_{1-4}$ alkyl radical, a divalent $C_{7-18}$ alkylaryl radical, or a divalent $C_{6-18}$ aryl radical.

4. The compound of claim 3 wherein Ar is an unsubstituted or inertly substituted bisphenylene radical.

5. The compound of claim 4 wherein L is selected from the group consisting of a direct bond, a divalent $C_{1-16}$ hydrocarbyl radical, and a divalent $C_{1-8}$ halohydrocarbyl radical.

6. The compound of claim 5 wherein r is an integer between 0 and 8.

* * * * *